US008734342B2

(12) United States Patent
Cable

(10) Patent No.: US 8,734,342 B2
(45) Date of Patent: May 27, 2014

(54) GRAPHICAL USER INTERFACE FOR IN-VIVO IMAGING

(75) Inventor: Michael D. Cable, Danville, CA (US)

(73) Assignee: Xenogen Corporation, Alameda, CA (US)

( * ) Notice: Subject to any disclaimer, the term of this patent is extended or adjusted under 35 U.S.C. 154(b) by 825 days.

(21) Appl. No.: 12/823,013

(22) Filed: Jun. 24, 2010

(65) Prior Publication Data

US 2010/0260395 A1   Oct. 14, 2010

Related U.S. Application Data

(63) Continuation of application No. 11/938,558, filed on Nov. 12, 2007, now Pat. No. 7,765,487, which is a continuation of application No. 10/458,579, filed on Jun. 9, 2003, now Pat. No. 7,299,420, which is a continuation of application No. 09/439,381, filed on Nov. 15, 1999, now Pat. No. 6,614,452.

(51) Int. Cl.
*A61B 5/00* (2006.01)
*G06F 19/00* (2011.01)
*G06T 7/00* (2006.01)

(52) U.S. Cl.
CPC ........... *G06F 19/321* (2013.01); *G06T 2200/24* (2013.01); *G06T 7/0012* (2013.01)
USPC ............................. 600/300; 382/132; 715/762

(58) Field of Classification Search
USPC ............ 600/300–301; 382/132; 715/762–764
See application file for complete search history.

(56) References Cited

U.S. PATENT DOCUMENTS

| 4,948,975 | A | | 8/1990 | Erwin et al. |
|---|---|---|---|---|
| 5,202,091 | A | | 4/1993 | Lisenbee |
| 5,319,209 | A | | 6/1994 | Miyakawa et al. |
| 5,414,258 | A | | 5/1995 | Liang |
| 5,431,161 | A | * | 7/1995 | Ryals et al. .................... 600/425 |
| 5,625,377 | A | | 4/1997 | Jenson |
| 5,636,299 | A | | 6/1997 | Bueno et al. |
| 5,637,874 | A | | 6/1997 | Honzawa et al. |
| 5,650,135 | A | | 7/1997 | Contag et al. |
| 5,672,881 | A | | 9/1997 | Striepeke et al. |

(Continued)

FOREIGN PATENT DOCUMENTS

| WO | WO 94/13095 | 6/1994 | ............. G06F 15/42 |
|---|---|---|---|
| WO | WO 00/17643 | 3/2000 | ............. G01N 33/53 |
| WO | WO 00/50872 | 8/2000 | ............. G01N 15/14 |

OTHER PUBLICATIONS

Collaborative Electronic Notebook Systems Association http://www.censa.org/, Downloaded Nov. 15, 1999).

(Continued)

*Primary Examiner* — Bill Thomson
*Assistant Examiner* — Bobby Soriano
(74) *Attorney, Agent, or Firm* — Fish & Richardson P.C.

(57) ABSTRACT

A graphical user interface is provided which allows the user to perform numerous operations suitable for analysis of in-vivo images within a single display screen or a single window. Using the in-vivo GUI, the user may create and manipulate analysis tools such as rectangle and ellipse tools to define regions of interest and perform various measurements on an in-vivo image. In addition, the GUI allows the user to store measurement results in a dated electronic notebook, display testing information, manipulate image presentation and print while maintaining view of the image.

15 Claims, 10 Drawing Sheets

(56) References Cited

U.S. PATENT DOCUMENTS

| | | | |
|---|---|---|---|
| 5,705,807 A | | 1/1998 | Throngnumchai |
| 5,722,405 A | * | 3/1998 | Goldberg ............... 600/407 |
| 5,738,101 A | | 4/1998 | Sappey |
| 5,740,267 A | | 4/1998 | Echerer et al. |
| 5,803,914 A | * | 9/1998 | Ryals et al. ............. 600/407 |
| 5,832,931 A | * | 11/1998 | Wachter et al. .......... 128/898 |
| 5,840,572 A | | 11/1998 | Copeland |
| 5,850,465 A | * | 12/1998 | Shimura et al. .......... 382/132 |
| 5,867,250 A | | 2/1999 | Baron |
| 5,970,164 A | | 10/1999 | Bamberger et al. |
| 6,030,344 A | * | 2/2000 | Guracar et al. ........... 600/447 |
| 6,058,322 A | * | 5/2000 | Nishikawa et al. ........ 600/408 |
| 6,081,612 A | | 6/2000 | Gutkowicz-Krusin et al. |
| 6,175,655 B1 | * | 1/2001 | George et al. ............ 382/257 |
| 6,217,847 B1 | | 4/2001 | Contag et al. |
| 6,242,743 B1 | | 6/2001 | DeVito et al. |
| 6,246,745 B1 | * | 6/2001 | Bi et al. ................. 378/54 |
| 6,272,233 B1 | * | 8/2001 | Takeo ................... 382/128 |
| 6,321,111 B1 | | 11/2001 | Perelman et al. |
| 6,332,038 B1 | | 12/2001 | Funayama et al. |
| 6,333,752 B1 | | 12/2001 | Hasegawa et al. |
| 6,364,829 B1 | | 4/2002 | Fulghum |
| 6,385,474 B1 | * | 5/2002 | Rather et al. ............ 600/407 |
| 6,563,942 B2 | * | 5/2003 | Takeo et al. ............. 382/132 |
| 6,614,452 B1 | | 9/2003 | Cable |
| 6,615,063 B1 | | 9/2003 | Ntziachristos |
| 6,633,657 B1 | * | 10/2003 | Kump et al. ............. 382/128 |
| 6,756,207 B1 | | 6/2004 | Guiliano et al. |
| 6,757,412 B1 | * | 6/2004 | Parsons et al. ........... 382/128 |
| 6,775,567 B2 | | 8/2004 | Cable |
| 6,949,081 B1 | * | 9/2005 | Chance ................. 604/67 |
| 7,003,161 B2 | * | 2/2006 | Tessadro ................ 382/199 |
| 7,113,217 B2 | | 9/2006 | Nilson et al. |
| 7,299,420 B2 | | 11/2007 | Cable |
| 2002/0012450 A1 | * | 1/2002 | Tsujii .................. 382/103 |
| 2002/0044691 A1 | * | 4/2002 | Matsugu ................ 382/218 |
| 2003/0193517 A1 | | 10/2003 | Cable |

OTHER PUBLICATIONS

E.C. Di Mauro, et al. "Check" A generic and specific industrial inspection tool, IEE Proceedings: Vision, Image and Signal Processing, Institution of Electrical Engineers, GB, vol. 143, No. 4, Aug. 1, 1996, pp. 241-249, XP000627046, ISSN: 1350-245X.

Electronic Notebooks http://labautomation.org/la/la2000/Courses/LA2000eln.htm (discussion of electronic notebooks available prior to Nov. 15, 1999).

Hamamatsu Corporation, USA, website, http://usa.hamamatusu.com/ pp. 1-4, Apr. 27, 2001, printed on Apr. 27, 2001.

Hamamatsu, Imaging Box Instruction Manual, 55310-224-1, Nov. 2000.

Mahmood et al., "Near-Infrared Optical Imaging of Protease Activity for Tumor Detection", Radiology, Dec. 1999, p. 866-870.

Office Action dated Jan. 17, 2007 in corresponding U.S. Appl. No. 10/458,579.

The FDA's final rule on electronic signatures and electronic records means to designers and users of automation systems—http://www.che.chalmers.se/acs-1v-97/cinf-59.html (Downloaded Nov. 15, 1999).

VetEquip Incorporated website, http://vetequip.com/1806.htm Table Top Laboratory Animal Anesthesia System, Apr. 27, 2001, printed on Apr. 27, 2001.

VetEquip Incorporated website, http://www.vetequip.com/impac.htm IMPAC$_6$ An anesthesia system designed for high volume, assembly-line type procedures, Apr. 27, 2001, printed on Apr. 27, 2001.

VetEquip incorporateed website, http://www.vetequip.com/1807.htm Mobile Laboratory Animal Anesthesia System, Apr. 27, 2001, printed on Apr. 27, 2001.

Weissleder et al., "Shedding Light onto Live Molecular Targets", Nature Medicine, vol. 9, No. 1, Jan. 2003, p. 123-1218.

Final Office Action dated Dec. 29, 2008 from U.S Appl. No. 11/006,294.

International Search Report dated Jul. 2, 2008 from PCT Application No. PCT/US05/43978.

Written Opinion of International Search Authority dated Jul. 2, 2008 from PCT Application No. PCT/US05/43978.

* cited by examiner

GRAPHICAL USER INTERFACE FOR IN-VIVO IMAGING

CROSS-REFERENCE TO RELATED APPLICATIONS

This application is a continuation of and claims priority under 35 U.S.C. §120 from U.S. patent application Ser. No. 11/938,558, filed Nov. 12, 2007, which is a continuation of and claimed priority under 35 U.S.C. §120 from U.S. patent application Ser. No. 10/458,579, filed Jun. 9, 2003, now U.S. Pat. No. 7,299,420 issued Nov. 20, 2007, which is a continuation of and claimed priority under 35 U.S.C. §120 from U.S. patent application Ser. No. 09/439,381 filed on Nov. 15, 1999, now U.S. Pat. No. 6,614,452 issued Sep. 2, 2003; each of these patent applications are hereby incorporated by reference in their entirety for all purposes.

FIELD OF THE INVENTION

The present invention relates generally to user interface software running on computers or computer systems. More specifically, the invention relates to user interface systems and methods used in examining and analyzing images.

BACKGROUND

In a computer application, there are numerous ways to present user information. Graphical user interfaces (GUIs) on computer systems allow easy use of windows, control icons, etc. to display information to the user. The data displayed in a window may be of different types. Some may be graphical, such as icons or pictures, or textual, such as a word processing document, or a combination of both.

When a computer interface is used for data management in a scientific application, the interface may include various data-specific tools and functions. To handle images, for example, an application might desirably present one or more windows for viewing the image, a tool for changing the image's appearance (e.g., sharpness), and a tool to measure features of one or more images.

Unfortunately, the unique combination of functionality required for many imaging applications is not provided in a simple and easy to use computer interface. Specifically, available user interfaces, even those developed to handle imaging applications, do not provide a suite of particular image presentation and analysis tools that allow users to manipulate and measure image features with minimal navigation through the user interface.

Interfaces for available applications typically require that the user first select or open various windows, menus, buttons, and/or tiles and then and then manipulate the resulting tool to implement a single operation pertinent to image analysis. Because the user may be required to perform numerous operations for a single image, or handle numerous images simultaneously, the available user interfaces are generally very awkward or unwieldy. Obviously this compromises user efficiency and effectiveness in evaluating images.

Specialized in-vivo imaging applications can present particular challenges to the design of an appropriate user interface. In one example, the image may include one or more representations of emissions from internal portions of a specimen superimposed on a photographic representation of the specimen. The photographic representation provides the user with a pictorial reference of the specimen. The luminescence representation indicates portions of the specimen where an activity of interest may be taking place. For example, the in-vivo data may include light emissions from specific regions of the specimen used in tracking the progression of tumor or a pathogen within the specimen.

In view of the foregoing, an improved user interface for imaging applications would be highly beneficial.

SUMMARY

The present invention addresses this need by providing a computer user interface having a window or other feature that provides tools allowing the user to quickly define a perimeter around a "region of interest" on the image and then measure a property of the image within the region of interest. The region of interest may be bounded by an ellipse, rectangle, or other shape selected and sized by the user. Preferably, both the image and the tool for generating the region of interest reside on the same window or other interface feature. Thus, a region of interest can be generated with one or two user interface actions (e.g., clicking on a button and then dragging a perimeter to an appropriate location on the image to specify the region of interest). The property measured within the region of interest may be an average or total pixel value within the region of interest.

In accordance with one embodiment of the present invention, a computer system is provided with an image measurement window, which allows the user to perform certain operations that are particularly useful for presenting and analyzing an image. In addition to having conventional computer hardware such as a processor, memory, and a display, the computer system includes a graphical user interface having a measurement window that provides both the image itself and one or more tools for defining a region of interest on the image. When a user uses one of the tools to define a region of interest, the computer system can calculate information about a portion of the image within the defined region of interest. By providing various frequently used features in a single window, interfaces of this invention remove the need to flip between alternate windows to take advantage of these features.

Among the other features that may be provided with the image measurement window is a measurement tool. When this tool is selected, the computer system automatically calculates the information about the portion of the image when the user uses one of the tools to define the region of interest on the image. The measurement window may also include display controls for controlling at least one the following features of the displayed image: threshold, brightness, contrast, and sharpness.

In a preferred embodiment, the one or more tools for defining the region of interest allows the user to graphically create a rectangle on the image, an ellipse on the image, and/or a grid on the image. At least one of these tools may be provided as a button which, when selected, causes a region of interest to appear on the displayed image. After the region of interest is created on the image, the user can move and/or reshape the region of interest by the action of the pointer.

In addition, the present invention may provide a date stamped electronic notebook in conjunction with the image measurement window. The electronic notebook may display image analysis data (typically text pertaining to the image) such as measurement results, experimental parameters, user notes, and the like. The computer system may automatically display and date stamp image measurement results obtained via the user interface.

In another aspect of the present invention provides a user interface for presenting and analyzing an image including a photographic representation of an object and a luminescence representation of the object. The luminescence representation presents the location and magnitude of radiation emitted from the object. The user interface may be characterized by the following features: (1) a first display control permitting a user to manipulate the visual presentation of at least one of the luminescence representation and the photographic representation; (2) a second display control permitting the user to create at least one region of interest on the luminescence representation; and (3) a third display control permitting the user to make a measurement of a portion of the luminescence representation bounded by the at least one region of interest. Other display controls of the user interface may include a fourth display control that permits the user to select which of the photographic representation and the luminescence representation is to be displayed. An optional fifth display control allows the user to print some portion or all of the image.

Yet another aspect of the present invention relates to a method implemented on a computer system. The method includes analyzing a region of interest on an image presented on a display associated with the computer system. This includes defining a region of interest on the image when the user has selected a region of interest tool from a user interface presented on the display. Note that the region of interest tool and the image are concurrently displayed on the display. The method further includes calculating a property of the image within the region of interest.

Embodiments of the present invention further relate to a computer readable medium including instructions for applying the above mentioned interfaces and methods. These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

In the following detailed description of the present invention, numerous specific embodiments are set forth in order to provide a thorough understanding of the invention. However, as will be apparent to those skilled in the art, the present invention may be practiced without these specific details or by using alternate elements or processes. In other instances well known processes, procedures, components, and circuits have not been described in detail so as not to unnecessarily obscure aspects of the present invention.

In accordance with one embodiment of the present invention, a graphical user interface (GUI) is provided which allows the user to perform numerous operations suitable for image analysis within a single window. This removes the need to navigate between alternate windows in order to perform a specific image analysis function. Using the GUI of this invention, the user may create and manipulate analysis tools and perform a wide variety of measurements on complex images (such as in-vivo images) conveniently and efficiently. In addition, the present invention may allow the user to store measurement results in a dated electronic notebook, display testing information, manipulate the image presentation and print while maintaining view of the image.

One preferred embodiment of this invention pertains to graphical user interfaces for presenting and analyzing "overlay" or "composite" images including a photographic image on which is overlaid an "emissions" image. The photographic and luminescence images are taken of the same object. In one application, the object is a biological specimen. The luminescence image is taken without using light sources other than the object itself. Luminescence from the object is recorded as a function of position to produce the luminescence image. One approach to generating such composite photographic/luminescence images is described in U.S. Pat. No. 5,650,135 issued to Contag et al. on Jul. 22, 1997. The entire disclosure of that patent is incorporated herein by reference.

Figure 1:
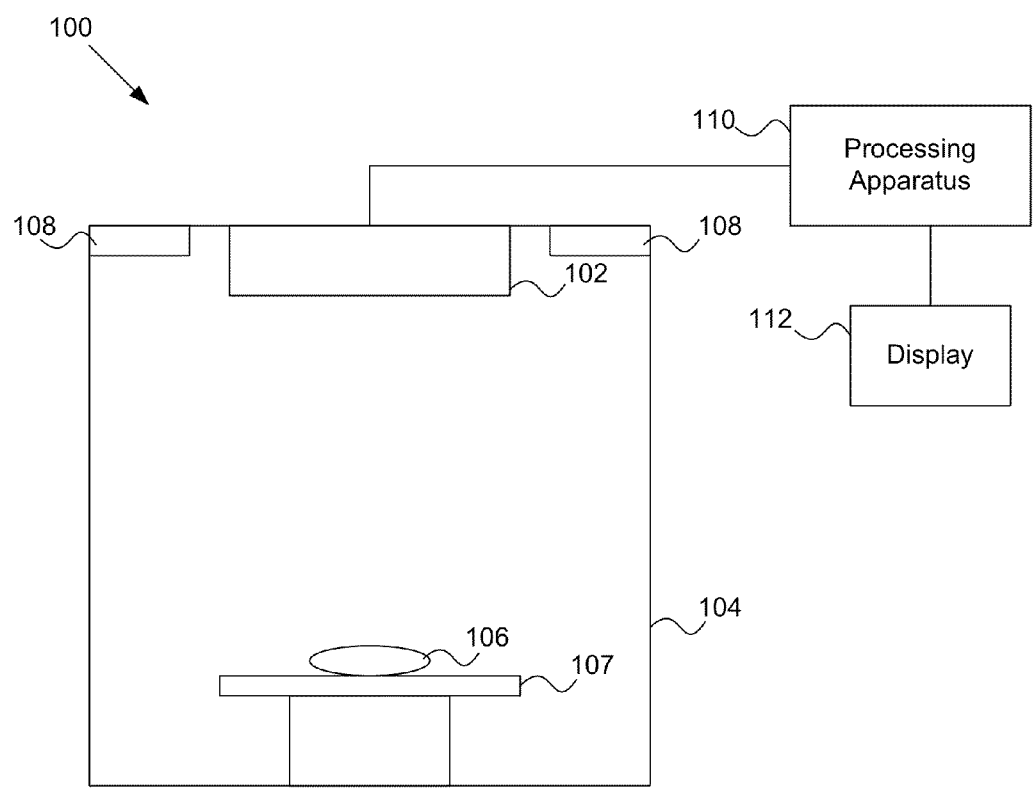
FIG. 1 illustrates an imaging apparatus suitable for capturing photographic and luminescence images in accordance with one embodiment of the present invention.

FIG. 1 illustrates an imaging apparatus 100 suitable for capturing photographic and luminescence images in accordance with one embodiment of the present invention. The imaging apparatus 100 includes a camera 102 such as a digital camera mounted at the top of a light-tight specimen box 104. The camera 102 is capable capturing photographic images (i.e., reflection based images) of a specimen 106. In addition, the camera 102 is sensitive enough to capture luminescence images of the specimen 106. Camera 102 may employ a charge coupled device (CCD), a photodiode array, a photogate array, or similar image capture device. To facilitate capturing photographic images, the imaging apparatus 100 includes lights 108. The lights 108 may be turned on or flashed while capturing photographic images of the specimen 106 and turned off while capturing luminescence images. The specimen box 104 may include a movable specimen platform 107 and other alignment instruments, which facilitates image capture of the specimen 106.

The camera 102 is in electrical communication with a processing apparatus 110. The processing apparatus 110 includes imaging hardware and other suitable processing hardware to permit processing of information obtained by the camera 102. By way of example, the processing apparatus 110 may include an I/O card, image processing logic, and control logic for controlling operation of camera 102 during image capture. The logic in apparatus 110 may take the form of software, hardware or some combination thereof. The processing apparatus 110 also communicates with a display 112. The display 112 presents the imaging information to the user. By way of example, the display 112 may be a monitor, which presents a image measurement GUI as outlined below.

Figure 2:
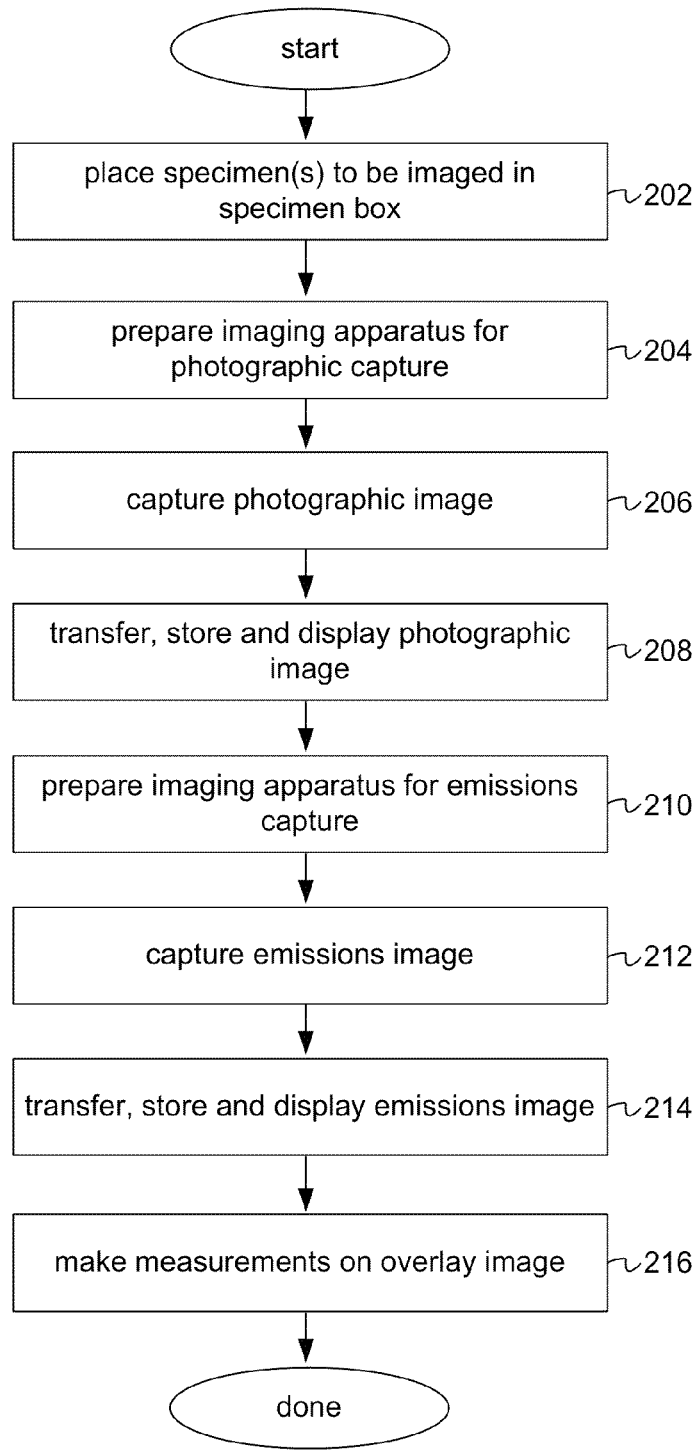
FIG. 2 is a flowchart illustrating a method of capturing photographic and luminescence images using the imaging apparatus of FIG. 1, for example, in accordance with one embodiment of the present invention.

FIG. 2 is a flowchart illustrating a method of capturing photographic and luminescence images using the imaging apparatus of FIG. 1, for example, in accordance with one embodiment of the present invention. A process flow 200 begins with placing the specimen 106 to be imaged in the imaging device (202). The imaging apparatus 100 is then prepared for photographic capture of the specimen 106 (204). The preparation may include turning on the lights 108, focusing the CCD camera 102, positioning the specimen 106, etc. After preparation, the photographic image is captured (206). In one imaging system suitable for use with the present invention, a 'live mode' is used in photographic capture of the specimen 106. The live mode includes a sequence of photographic images taken frequently enough to simulate live video. Upon completion of photographic capture, the photographic image data is transferred to processing apparatus 108 (208). The processing apparatus may manipulate and store the photographic image data as well as present it on the display 112.

Subsequently, the imaging apparatus 100 is prepared for capturing a luminescence image (210). The preparation may include turning off the lights 108, for example. When ready, the CCD camera 102 captures the luminescence image. The luminescence image data is transferred to the processing apparatus 108 (212). The processing apparatus may store and manipulate the luminescence image data as well as present it on the display 112 (214). The manipulation may also include overlaying the luminescence image with the photographic image and illustrating the two images together. This overlay image may then be the basis for user analysis (216).

At this point, the user now has the components of a digital overlay image stored in the processing apparatus 110 including the luminescence image and the photographic image. The information contained in the digital overlay image may be analyzed and manipulated as desired. As explained, the photographic and luminescence representations provided by the imaging apparatus 100 and imaging interface of the present invention have a wide variety of applications.

In one particular embodiment, the luminescence representation indicates the number of times each detector pixel has received a photon over a defined length of time. In other words, the luminescence representation may display magnitude values representing the photon counts at the individual detector pixels. Regions of the object emitting radiation (e.g., photons) will appear in the luminescence representation. The luminescence images may indicate the presence of a biocompatible entity, for example. The entity can be a molecule, macromolecule, cell, microorganism, a particle or the like. Thus, an in-vivo analysis may include detecting localization of a biocompatible entity in a mammalian subject. Alternatively, the information in the live mode may be used to track the localization of the entity over time. For more examples of analysis applications for a digital overlay image suitable for use with the present invention, the reader is referred to in U.S. Pat. No. 5,650,135, which was previously incorporated by reference.

Figure 3A:
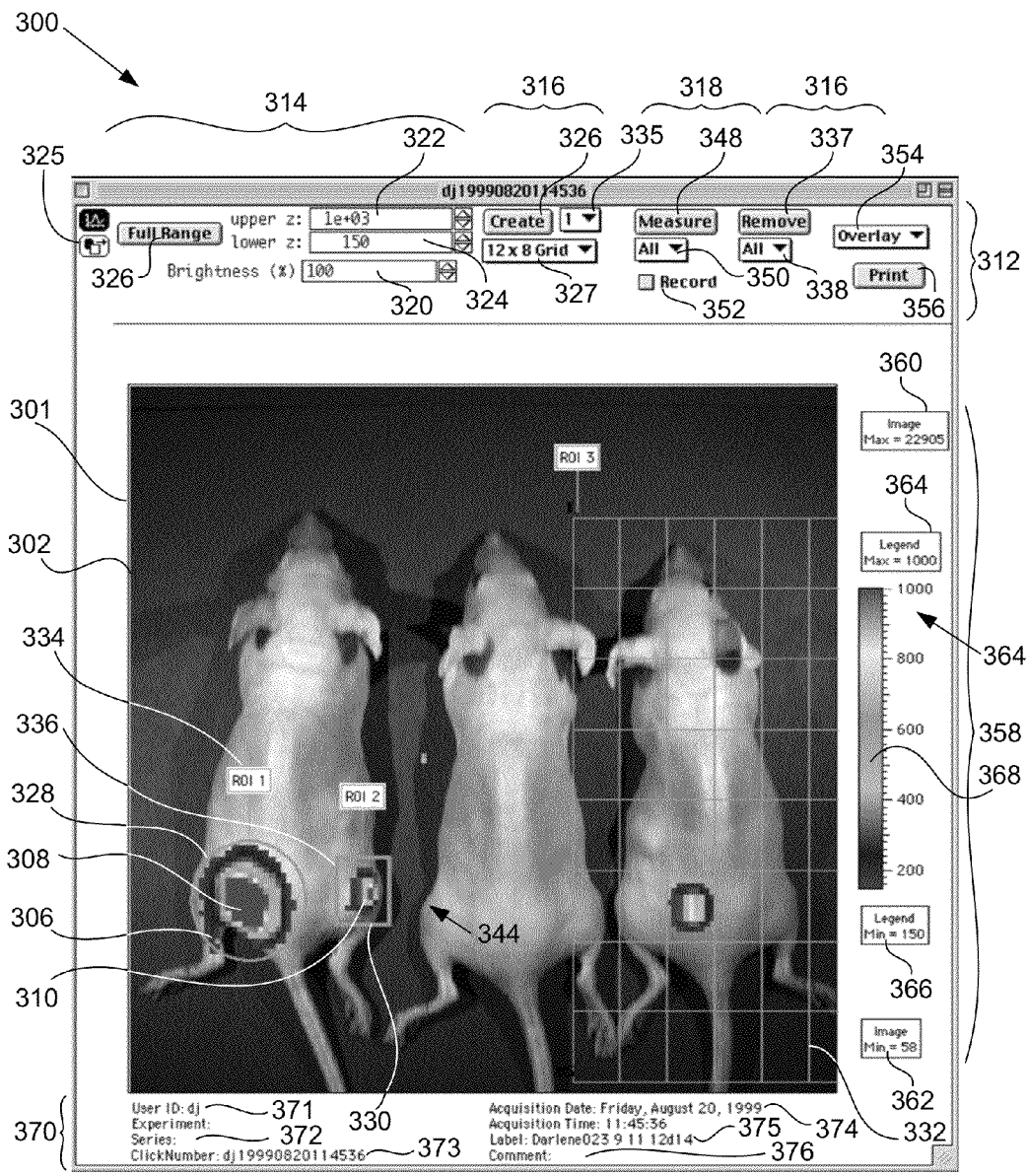
FIG. 3A is an illustration showing a graphical user interface having an overlay of a photographic representation and a luminescence representation of a specimen as well as various image manipulation, analysis and measurement tools.

FIG. 3A illustrates one example of an image control/measurement window 300 in accordance with this invention. The image control window 300 includes an image measurement window 301. Within the image measurement window 301, an overlay image 302 is displayed. The overlay image 302 includes a visual superposition of a photographic representation of the specimen 106 and a luminescence representation of the specimen 106. In this example, the specimen comprises three mice. The image control window 300 is well suited for manipulating the display of the overlay image 302 as well as making measurements and analyzing the luminescence representation.

The photographic representation provides the user with a visual frame of reference of the image. The luminescence representation provides photon emission data derived from the object. As mentioned, the photon emission data may represent the specific pixels on the CCD camera 102 that detect photons over the duration of the live mode image capture period. Because the imaging apparatus 100 is typically used to measure the entire specimen 106, the data in the luminescence representation typically has one or more distinct luminescent portions of interest. For example, the luminescence representation includes luminescent portions 308 and 310.

Although the image control window 300 displays an overlay image 302 comprised of two separate representations, most data manipulation and analysis of interest is performed on the luminescence representation. In particular, an analysis may include a summation of the illumination magnitudes over the pixels within a portion of the luminescence representation. Note that although the discussion will focus on a single luminescence representation for the overlay image 302, the image control window 300 may include multiple luminescence representations taken at different times.

In the illustrated embodiment, image control/measurement window 300 includes a control panel 312. The control panel 312 includes a plurality of user interface control components for facilitating manipulation and analysis of information in the image measurement window 301. To facilitate discussion, the user interface control components may be grouped into functional sections within the control panel 312. As illustrated, the control panel 312 includes a display function section 314, a create function section 316 and a measurement function section 318. Other arrangements, with or without a "control panel" are contemplated. The display function section 314 includes controls for allowing the user to manipulate the presentation of the photographic representation and the luminescence representation. To manipulate the presentation of the photographic representation, the display function section 314 includes a brightness setting 320. The brightness setting 320 is used for improving the user's visual perception of the photographic representation by allowing adjustment of the photograph's brightness. In alternative embodiments, other controls on a photographic image such as contrast, sharpness, and the like may be provided.

To manipulate the presentation of the luminescence representation, the display function section 314 includes an upper luminescence limit 322 and a lower luminescence limit 324. The upper luminescence limit 322 allows the user to designate the maximum data value displayed in the luminescence representation. Any pixels within the luminescence representation having a data value (e.g., a photon count) at or over this upper luminescence limit 322 will be displayed with a color corresponding to the upper luminescence limit 322. Similarly, the lower luminescence limit 324 allows the user to designate the minimum data value displayed in the luminescence representation. Any pixels within the luminescence representation having a data value below this lower luminescence limit 324 will not be displayed. Those pixels having a data value at the lower luminescence limit will be displayed with a color corresponding to the lower luminescence limit. Thus, the upper and lower luminescence limits specify the range of pixel illumination values over which the full range of display colors will be vary. The upper luminescence limit 322 and the lower luminescence limit 324 may be useful when the user wants to selectively clear the image of outlying data for a particular analysis. Alternatively, the lower luminescence limit 324 may be useful when the user wants to clear the image of noise.

The display function section also includes a global setting 326. The global setting 326 provides a default option for the presentation of the luminescence representation. Specifically, the global setting sets the upper luminescence limit 322 and lower luminescence limit 324 to specified values. In a preferred embodiment, the upper luminescence limit 322 and lower luminescence limit 324 are set to the 'full range' of values for the luminescence representation. In other words, the upper limit is set to the value of the maximum intensity measured for any pixel in the luminescence representation and the lower limit is set to the value of the minimum intensity measured for any pixel in the luminescence representation. Alternatively, another preset option may set the upper luminescence limit 322 and lower luminescence limit 324 to a standardized range of values for the luminescence representation. For example, the standardized range may set the upper luminescence limit 322 at 95% of the maximum photon count for the luminescence representation and the lower luminescence limit 324 at 5% of the maximum photon count. Alternatively, another standardized range may be based on a statistical analysis, such as the standard deviation, of the range of data values for the luminescence representation.

Often, it is desirable to calibrate the photographic representation and the luminescence representation to a blank view of the light-tight specimen box 104 without the specimen 106. The image for an blank view of the light-tight specimen box 104 without the specimen 106 is often referred to as a 'dark image'. The dark image may indicate inherent defects in a solid state camera, which defects should be subtracted from images taken with the camera. For example, the dark image may show contain bright spots corresponding to camera pixels having a high leakage current. To allow correction for such defective pixels, the display function section 314 may include a background compensation tool 325. When a user selects the background compensation tool 325, the computer system alters the photographic representation and the luminescence representation to compensate for any information associated with the dark image.

The create function section 316 includes controls for allowing the user to create and manipulate tools which enable simple and flexible analysis of the data within the image measurement window 301. In the specific embodiment depicted, the create function section 316 includes a create button 326. The create button 326 allows the user to create a region of interest (ROI) with one action on the interface. For example, the user simply clicks on button 326 with a pointer and a new ROI appears in the image measurement window. The ROI may be any geometric shape or tool for measuring and analyzing data in a portion or portions of the luminescence representation. To facilitate generation of ROIs, the create function section 316 includes a pop-up menu 327. The pop-up menu 327 includes a number of ROIs commonly used for image analysis. For example, the create button 326 and pop-up menu 327 may allow the user to create an ellipse (circle) 328, a rectangle (square) 330 or a grid 332. Upon creating an ROI, a label may be attached to the geometric outline of the ROI for user clarity. In FIG. 3A, for example, a label 334 is attached to circle 328.

To manage multiple ROIs, the create function section 316 includes a designation pop-up menu 335. The designation pop-up menu 335 lists and numbers the ROIs as they are created. In addition, the designation pop-up menu 335 allows the user to re-access previously created ROIs that were previously numbered and stored. Typically, the ROI currently being accessed by the user is indicated to the user via highlights 336. The create function section 316 also includes a remove tool 337. The remove tool 337 allows the user to delete any or all of the ROIs stored in the designation pop-up menu 336. The remove tool 337 may also include a pop-up menu 338 for convenience in deleting the ROIs.

The image control window 300 also allows the user to manipulate the ROIs. Thus, after the circle 328 is dragged to its desired position, the size, shape, position and orientation of the circle 328 may be altered. For example, the orthogonal axis of the circle 328 may be altered to form an ellipse. The ellipse may then characterized by a major axis and a minor axis. Similarly, the dimensions of the square 330 may be altered to form a rectangle. The manipulation of the ROIs may further include rotations, expansions, etc. In one embodiment, the dragging of an ROI is done by clicking a pointer 344 on a portion of the circle 328. Alternatively, the reshaping of an ROI may be performed by clicking the pointer 344 on one of the highlights 346 and dragging. In another embodiment, the manipulation and alterations of the ROIs may include keyboard input.

While the image control window 300 only shows three ROI options, there are a large number of alternative ROI configurations which may be implemented. By way of example, the ROI options may be include a free-hand drawing option, polygons of five or more sides, curve drawing options, and the like. In the free-hand drawing option, the user marks a series of points, which then form a perimeter of a closed ROI. Using the created ROIs, the user may then proceed to use one or more of the ROIs to measure and analyze data.

The measurement function section 318 includes GUI controls for allowing the user to measure and analyze data within the image measurement window 301. The illustrated measurement function section 318 includes a measure button 348. The measure command allows one or more functions for analysis of the data in the luminescence representation. By way of example, one function may be summation of all the pixel magnitudes within the perimeter of one or more of the ROIs. Another function may include an average of the magnitudes over the area within an ROI. Yet another function may also be a statistical analysis of the data within one or more of the ROIs.

To increase measurement flexibility, the measurement function section 318 includes a measurement designation pop-up menu 350. The measurement designation pop-up menu 350 enables the user to specify which of the created ROIs stored in the designation pop-up menu 335 are to be included in a measurement. Correspondingly, the user may specify any or all of the previously created ROIs for a particular measurement.

The measurement function section 318 also includes a record option 352. The record option 352 allows the user to store the data produced from the measure command 348. In one embodiment, the data is stored in an electronic notebook. The electronic notebook is an on-line tool which allows testing results and information to be stored automatically and will be described further with respect to FIG. 3B.

The image control window 300 also includes numerous other user interface tools. For example, a global display tool 354 is included to allow the user to control which representations are displayed in the measurement window 301. More specifically, the user may select the overlay image 302 including the visual superposition of the photographic representation and the luminescence representation. Alternatively, using the global display tool 354, the user may select just one of the photographic representation and the luminescence representation. The global display tool 354 may also allow the user to select between numerous luminescence representations stored for the photographic representation. The global display tool 354 typically has a default setting when a data file is accessed. For the image control window 300, the default setting is the overlay image 302 comprising the photographic representation and one luminescence representation.

On the right side of the image control window 300 is a luminescence image display section 358. The luminescence image display section 358 includes a number of components to assist in viewing and comprehension of the luminescence representation. The luminescence image display section 358 includes an image maximum 360 and an image minimum 362. The image maximum 360 indicates the magnitude of the highest data value (photon count) for any pixel in the luminescence representation. The image minimum 362 indicates the magnitude of the lowest data value (photon count) for any pixel in the luminescence representation. The difference between the image maximum 360 and the image minimum 362 corresponds to the full range of pixel magnitudes for the luminescence representation.

The luminescence image display section 358 also includes a legend maximum 364 and legend minimum 366. The legend maximum 364 indicates the magnitude of the maximum data value (photon count) for the image measurement window 301. In other words, the legend maximum 364 corresponds to the upper luminescence limit 322. The legend minimum 366 indicates the magnitude of the minimum data value for the image measurement window 301, similarly corresponding to the lower luminescence limit 324. Thus, if the full range is selected in the global setting 326, the legend maximum 364 and the legend minimum 366 may correspond to the image maximum 360 and the image minimum 362. The legend maximum 364 indicates the magnitude of the highest data value (photon count) in the luminescence representation that will be displayed with the highest intensity color (e.g., red). Any pixels having an intensity magnitude of greater than or equal to the highest data value will be given the highest intensity color. The legend minimum 366 indicates the magnitude of the lowest data value (photon count) in the luminescence representation that will be displayed with the lowest intensity color (e.g., blue).

Included in the image display section 358 is a scale 364. The scale 364 provides a visual mapping between a range of colors for the luminescence representation and the magnitude range specified at 322 and 324. For the image control window 300, the scale may be represented by a gray scale and thus individual magnitudes correspond to shades of gray or by color and thus the magnitude indicator correspond to different colors.

The image control window 300 also includes a user information section 370. The user information section 370 provides testing information for the overlay 302, which may be helpful to the user. The testing information may include, for example, a user ID 371, a test classification 372, a testing reference number 373, a date 374, a label 375 and a comments field 376.

A print button 356 is also included and allows the user to conveniently print portions of the image control window 300. Typically, the print button 356 employs a default setting corresponding to preferred use. For the image control window 300, the default setting automatically prints the image measurement window 301, the luminescence image display section 358 and the user information section 370. Alternatively, the print command 356 may introduce a settings window to set the default print options.

Although the present invention has been discussed primarily in the context of manipulating simple two-dimensional images, the analysis tools and methods of the present invention are also suitable for more complicated applications. By way of example, to compensate for different sized specimens or images at varying depths, the imaging apparatus 100 may take alternate luminescence images of the specimen 106. More specifically, to overcome dependency on the depth of the image, different wavelengths may be used in capturing the luminescence image.

Figure 3B:
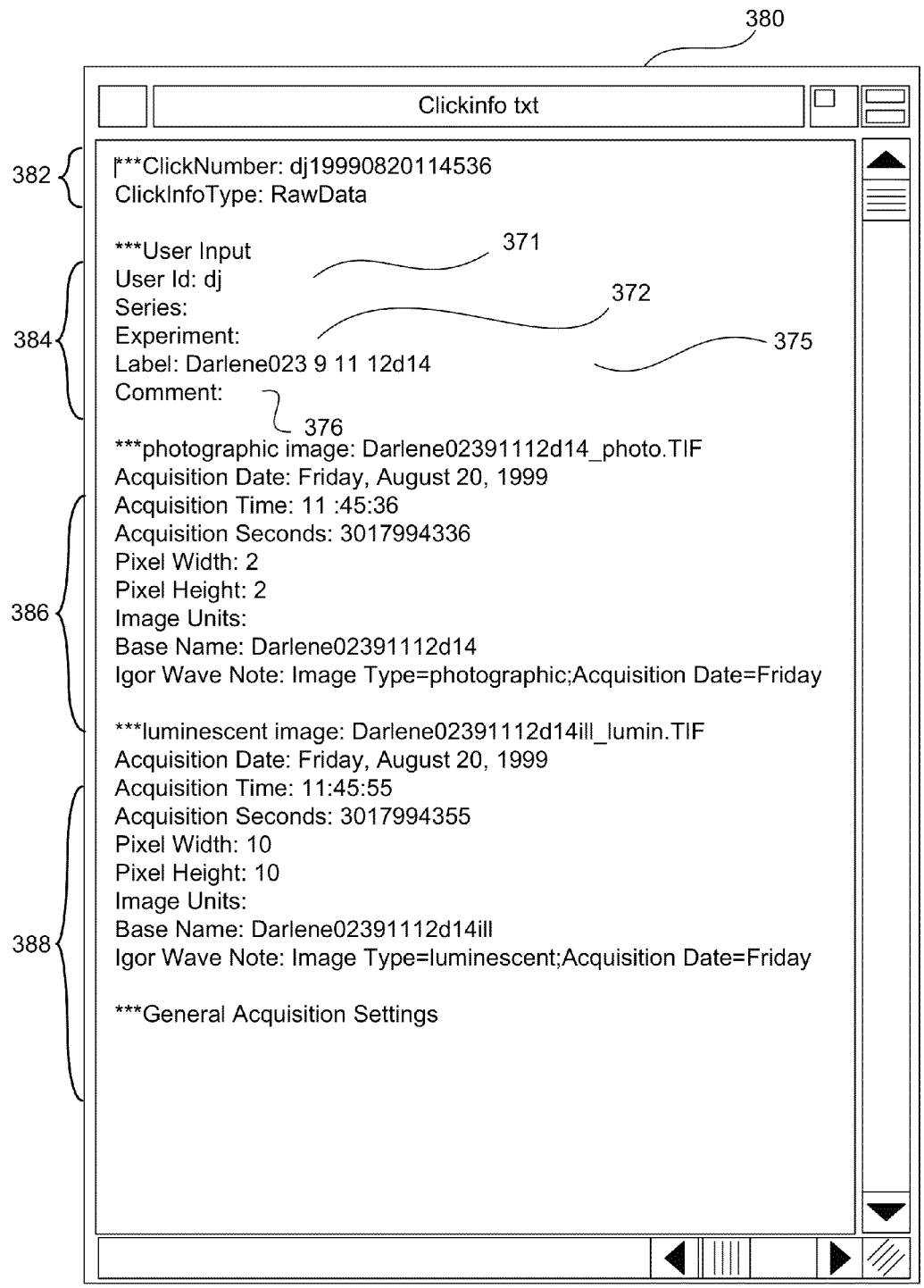
FIG. 3B illustrates an electronic notebook page suitable for storing raw data and non-analysis information in accordance with one embodiment of the present invention.

As mentioned previously, the present invention may implement an electronic notebook. The electronic notebook allows the user to automatically store analysis data, ROI settings, measurement results and conveniently perform other useful note taking functions. FIG. 3B illustrates an electronic notebook page 380 in accordance with one embodiment of the present invention. In this case, the notebook page 380 appears as a separate window to the side of the image control window 300.

The electronic notebook page 380 may automatically store information corresponding to the overlay image 302 upon instantiation. By way of example, the electronic notebook page 380 may be instantiated when the user initially loads an image. In this case, image capture information will be entered first. Alternatively, the electronic notebook page 380 may be instantiated when the user creates an ROI for the first time or inputs any information, which is relevant to an analysis of the luminescence representation. In addition, if the overlay image 302 is accessed from memory, the electronic notebook page 380 may be instantiated as last saved.

In one embodiment, the electronic notebook page 380 solely contains reference information corresponding to the overlay image 302 and does not include analysis information and results. In this case, the electronic notebook page 380 is referred to as a 'raw data' page. The electronic notebook page 380 may include a header 382. The header contains classification information for the overlay image 302 such as the testing reference number 373. The electronic notebook page 380 may also include a user input section 384. The user input section 384 may include, for example, the user ID 371, test classification 372, the label 375 and comments field 376 corresponding to the user information section 370 of the image control window 300. Alternatively, the user may enter information into the notebook page 380 as desired.

The electronic notebook page 380 may also include other information used in characterizing data or an image. For example, a photographic image section 386 includes information relevant to the settings used for photographic image capture using the imaging apparatus 100. In addition, an luminescence image section 388 includes information relevant to the settings used for luminescence image capture using the imaging apparatus 100.

For user convenience, the electronic notebook page 380 may be saved in a database which stores all the raw data files and corresponding image files in a common directory. In one embodiment, this database for raw data files is referred to as a 'raw data set'. More specifically, the database may be arranged such that a text file is associated with each image file in the data set. The text file may contain information about the image captured. By way of example, the image information may include the time the image was taken, the camera settings (i.e. the exposure length), image identification numbers, labeling information entered by the user when the image was taken. In addition, each photographic representation and luminescence representation may have its own file in the raw data set.

Preferably, the file formats used in the raw data set are generic to increase application flexibility. By way of example, the photographic representation and luminescence representation may be saved in a TIFF format to allow access from a wide variety of software packages. Similarly, each text file may be saved as an ASCII text file to allow flexible access. Thus, a raw data database may be established which is generic and easily accessible.

Figure 3C:
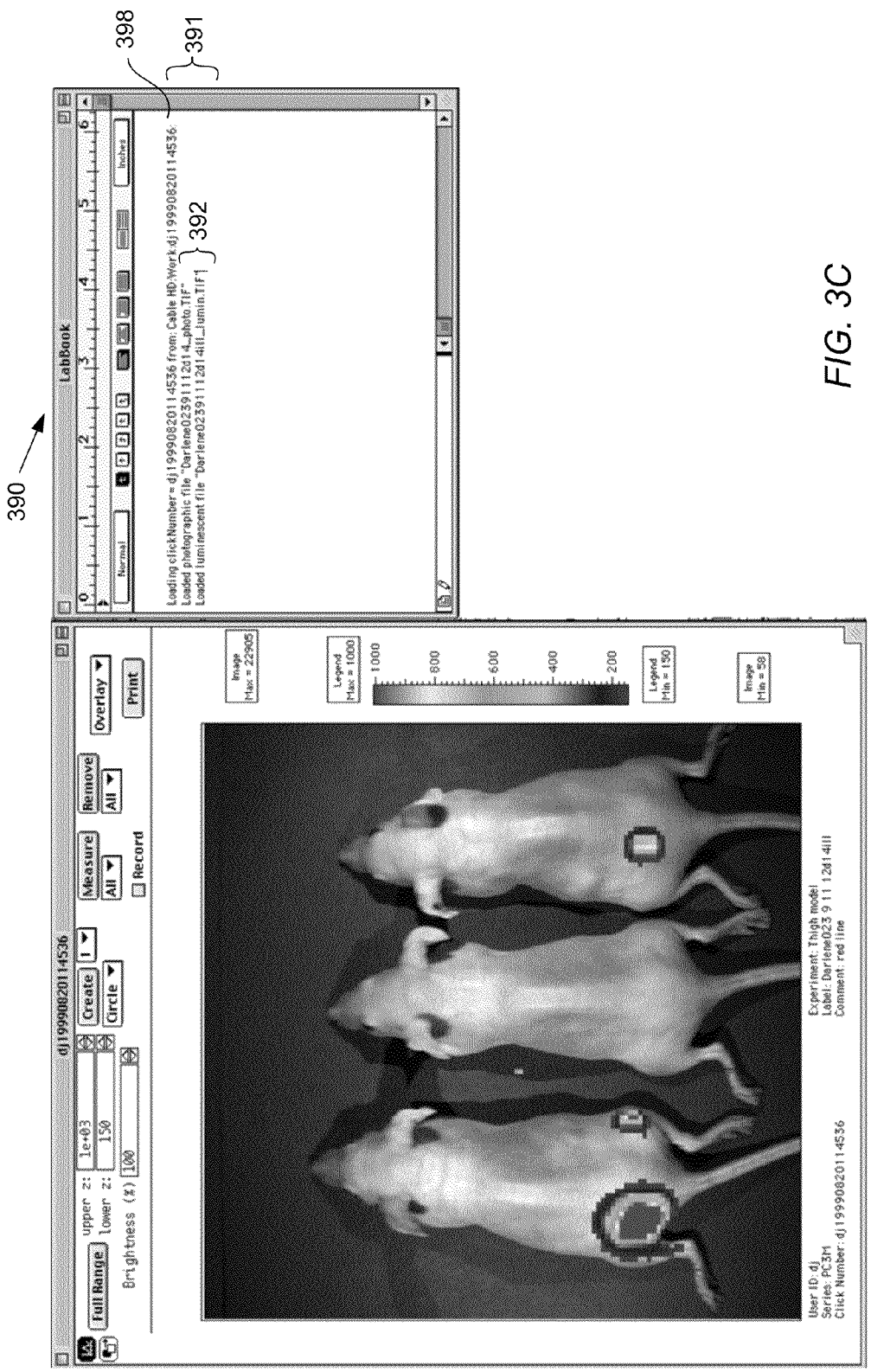
FIGS. 3C-E illustrate the automatic storage of analysis data and measurement results into an electronic notebook page in accordance with another embodiment of the present invention.
Figure 3D:
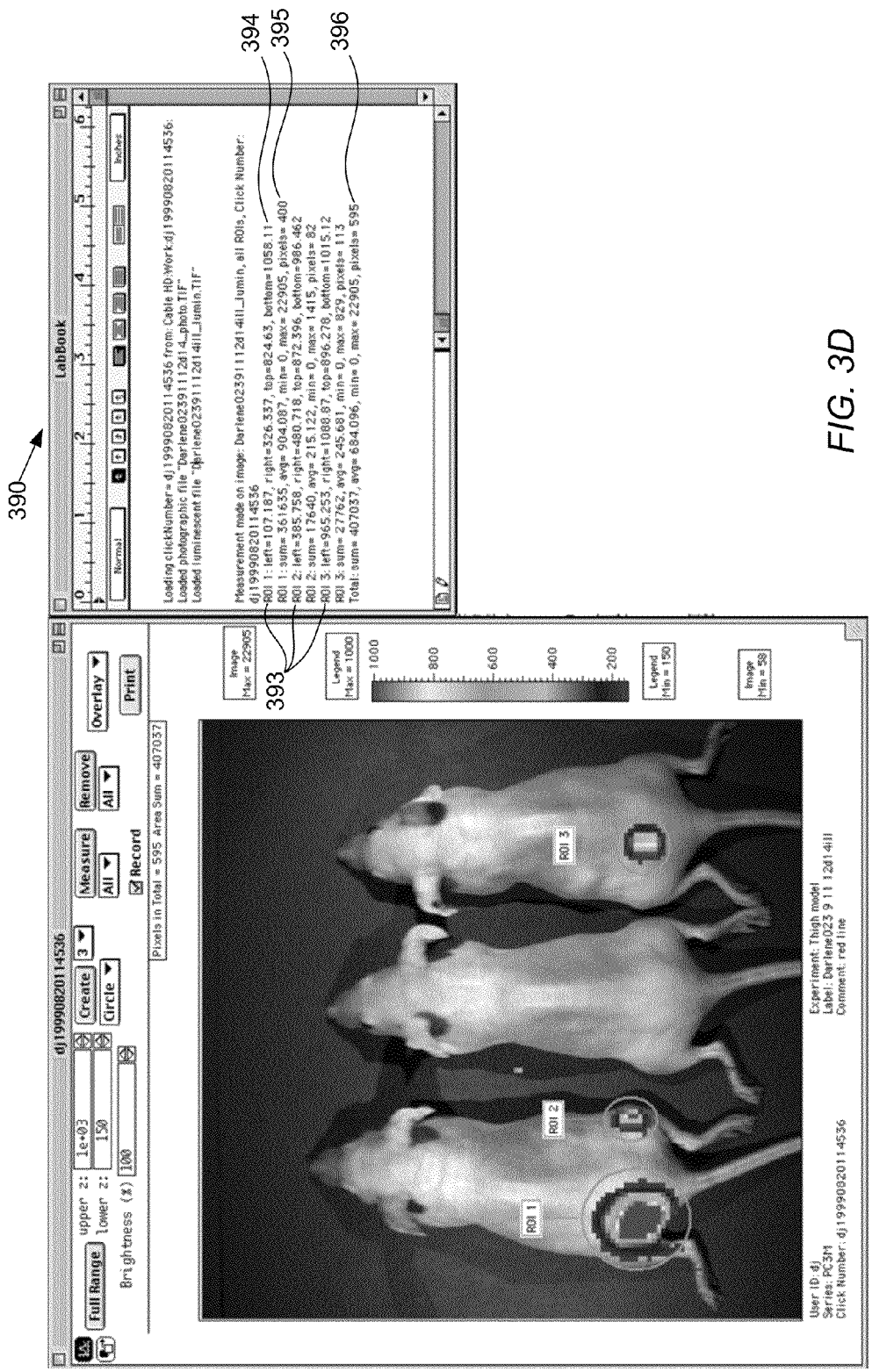
Figure 3E:
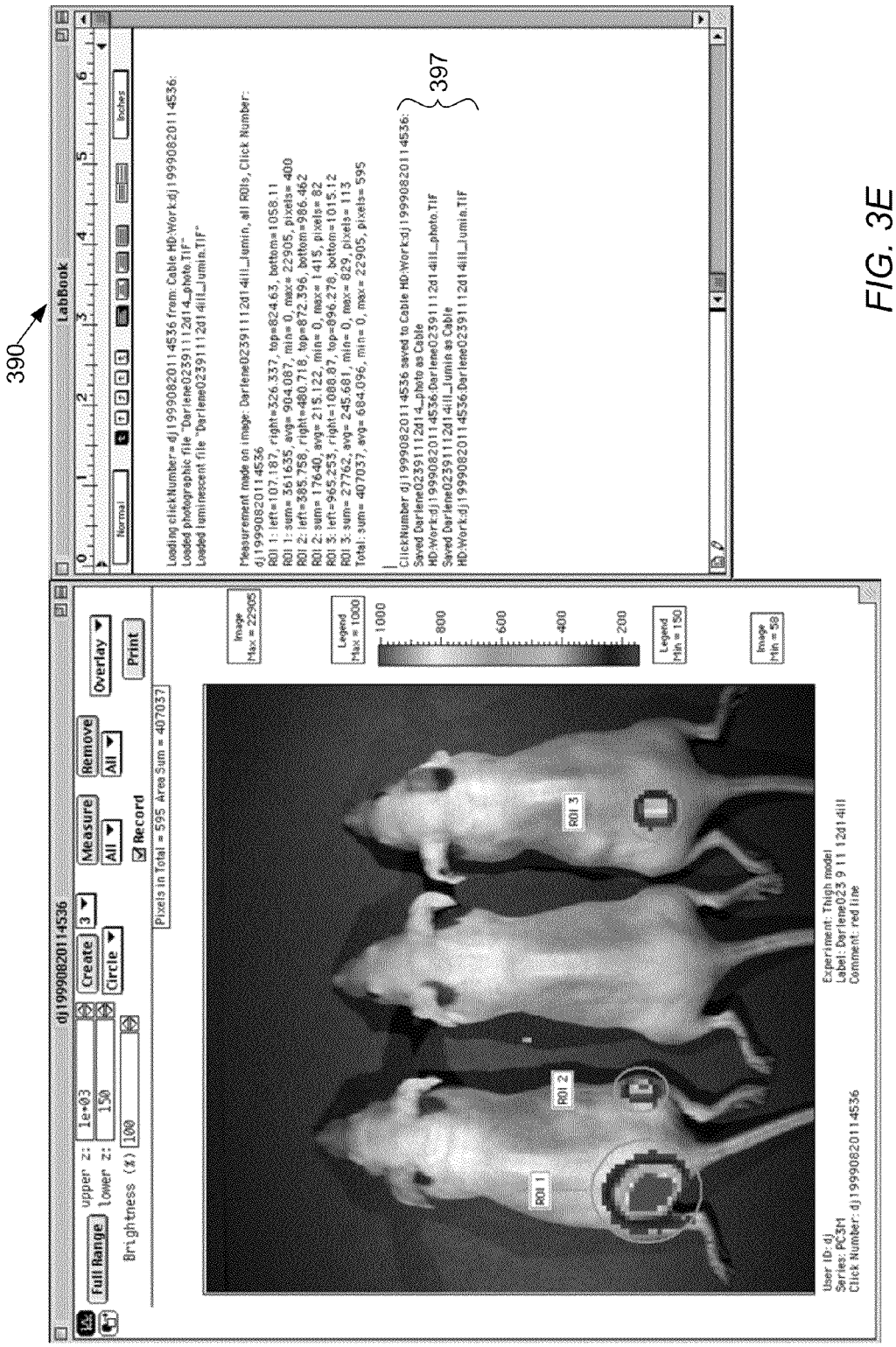

In another embodiment, an electronic notebook page may contain information that includes analysis settings and measurement results. FIGS. 3C-E illustrate the automatic storage of analysis data and measurement results into an electronic notebook page 390 in accordance with another embodiment of the present invention. In this case, the electronic notebook page 390 is referred to as a 'analyzed data' page. In a preferred embodiment, the electronic notebook automatically stores the analysis data 382 obtained from the measure command 348 when the record option 352 is selected. Storing the analysis data provides the user a convenient mechanism to access the analysis data at a subsequent time. The analysis data may include the characteristic geometric information of the ROIs as well as the results of any measurements using the ROIs.

FIG. 3C illustrates the electronic notebook page 390 before analysis information is entered. In this case, the header 391 includes a testing reference 398 and file references 392. The testing reference 398 includes the analysis date in the first six numerical digits, the user name and may also include other testing information. In one embodiment, the electronic notebook page 390 automatically records an automatic date stamp in which an analysis was performed in the testing reference 398. The automatic date stamp may be advantageous in the future for verifying the date of analysis and testing. In one embodiment, the automatic date stamp is subsequently unalterable to further strengthen subsequent validation. The file references 392 refer to data files which includes the loading information of the photographic representation and the luminescence representation. The file references 392 may also include the information relevant to the settings used for photographic and luminescence image capture using the imaging apparatus 100.

FIG. 3D illustrates the electronic notebook page 390 after an analysis using three ROIs 393. For each ROI, its characteristic geometric information 394 regarding the perimeter of the ROI is automatically stored in the electronic notebook page 390. In addition, results 395 for the measurement within each ROI 393 are automatically stored. Further, total measurement results 396 for all three ROIs are automatically stored. FIG. 3E illustrates the electronic notebook page 390 prior to exiting the image control window 300.

At this point, filing information 397 may be stored prior to closing of the electronic notebook page 390 (FIG. 3E). In addition, the electronic notebook page 390 allows the user to make notes and input additional analysis information at any time. Preferably this is accomplished by simply placing the cursor/pointer at the desired location within the electronic notebook and typing in the notes of interest. By way of example, statistical information for the luminescence representation such as a number of pixels 398 in the ROIs, area sums 399 and standard deviation, etc. may be stored if they are not included in the automatic transfer of information from the image control window 300. Alternatively, luminescence representation information such as the image maximum 360, image minimum 362 and average data value per pixel may be stored in the electronic notebook page 390. Broadly speaking, the electronic notebook page 390 may store any information relevant to re-creating a measurement or analysis.

In addition to the raw data set, a directory may be maintained for the electronic notebook page 390 and similar other analyzed data files. In one embodiment, this analyzed file directory is referred to as an 'analyzed data set'. Thus, two databases may be maintained: the first containing raw data and the second containing analyzed data. In one embodiment, the files stored in the analyzed data set will contain information about the photographic representation, the luminescence representation and the text file corresponding to the analyzed data all in one file. The file may be any such format which allows these pictorial and text components. By way of example, the file may be a Living Image file suitable for use with the Living Image Software.

Figure 4:
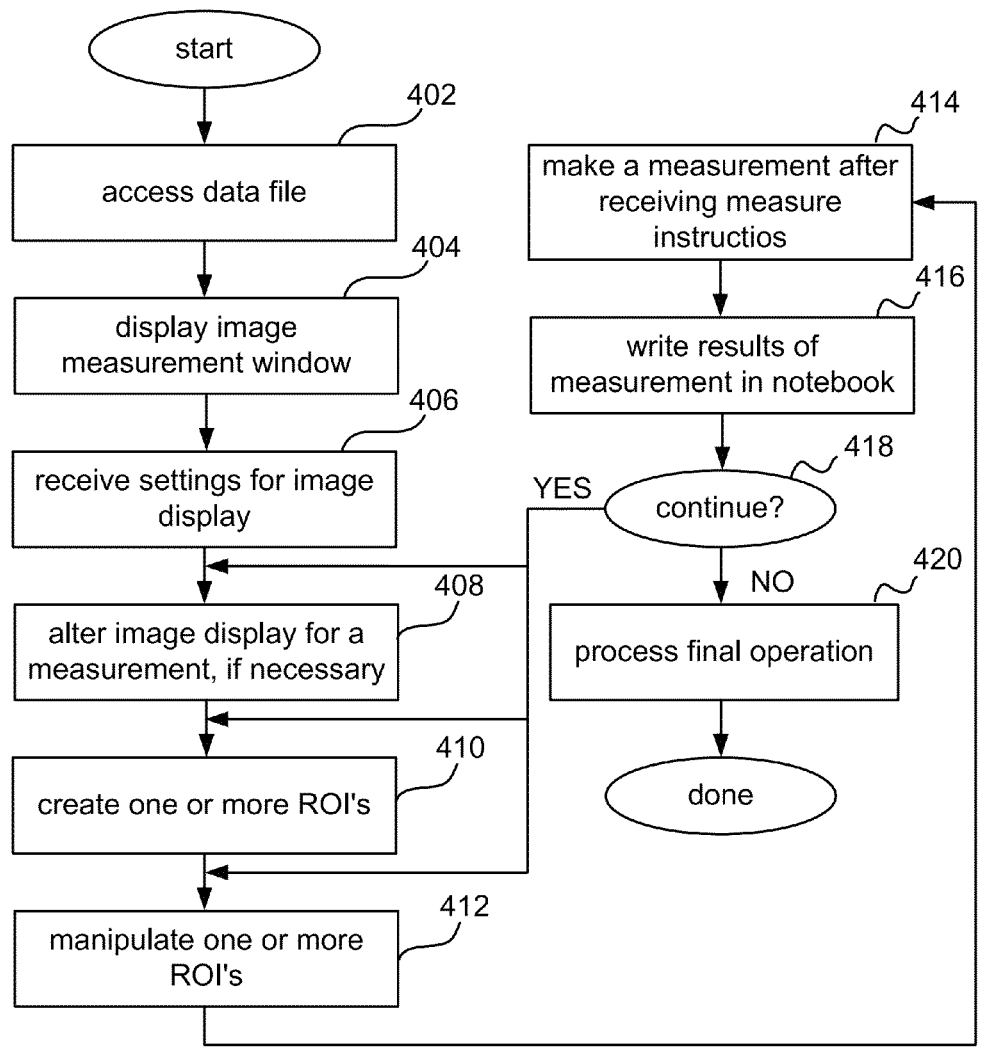
FIG. 4 is a flowchart illustrating a method of making measurements using the GUI of FIG. 3 in accordance with one embodiment of the present invention.

FIG. 4 is a flowchart representative of an exemplary data analysis using the image control window 300. A process flow 400 typically begins with accessing a data file (402). Accessing the data file may include opening a data file previously stored in memory. Alternatively, the data file may be accessed from an image recently captured by the imaging apparatus 100, without opening a stored file.

After the image measurement window 301 for the data file is displayed (404), the user may alter the photographic representation and the luminescence representation using any of the tools in the display function section 314 (406). By way of example, the user may alter the upper luminescence limit 322 and lower luminescence limit 324 to facilitate viewing clarity and comprehension of the image. For an initial use of an image, the user may also enter details in the user information section 370. In addition, the user may proceed to further alter the image display (408). By way of example, the user may alter the luminescence limit 322 and lower luminescence limit 324 to facilitate viewing clarity of a particular portion of the luminescence representation to be analyzed.

Upon determining which portion or portions of the luminescence representation are to be analyzed, the user may then create one or more ROIs (410). After the corresponding ROIs are generated, the user may alter the generic ROIs for a particular analysis (412). More specifically, the user may manipulate the position, shape and angle of rotation of one or more created ROIs. Upon completion of ROI manipulation, the user may then perform a measurement within one or more of the ROIs (414). In a preferred embodiment, the measurement involves taking a summation of the photon counts for each of the pixels within the perimeter of one or more ROIs. The results of the measurement may then be transferred to the electronic notebook page 390 (416).

The user may then continue (418) to make measurements on the same or different portions of the luminescence representation using the image control window 300. Correspondingly, the user may return to alter the image display for another measurement (408), create more ROIs (410) or manipulate the existing ROIs (414). If the user is finished with analysis on the current image, then the user may save the work and exit (420). It should be noted that the flowchart 400 is one method of using the image control window 300 for analysis of the overlay image 302. Obviously, many of the elements of the flowchart 400 may be repeated or performed outside of the order illustrated. By way of example, at any point the user may alter the image display to improve viewing (408), print the image control window 300 or make notes in the electronic notebook page 390 (418).

Figure 5:
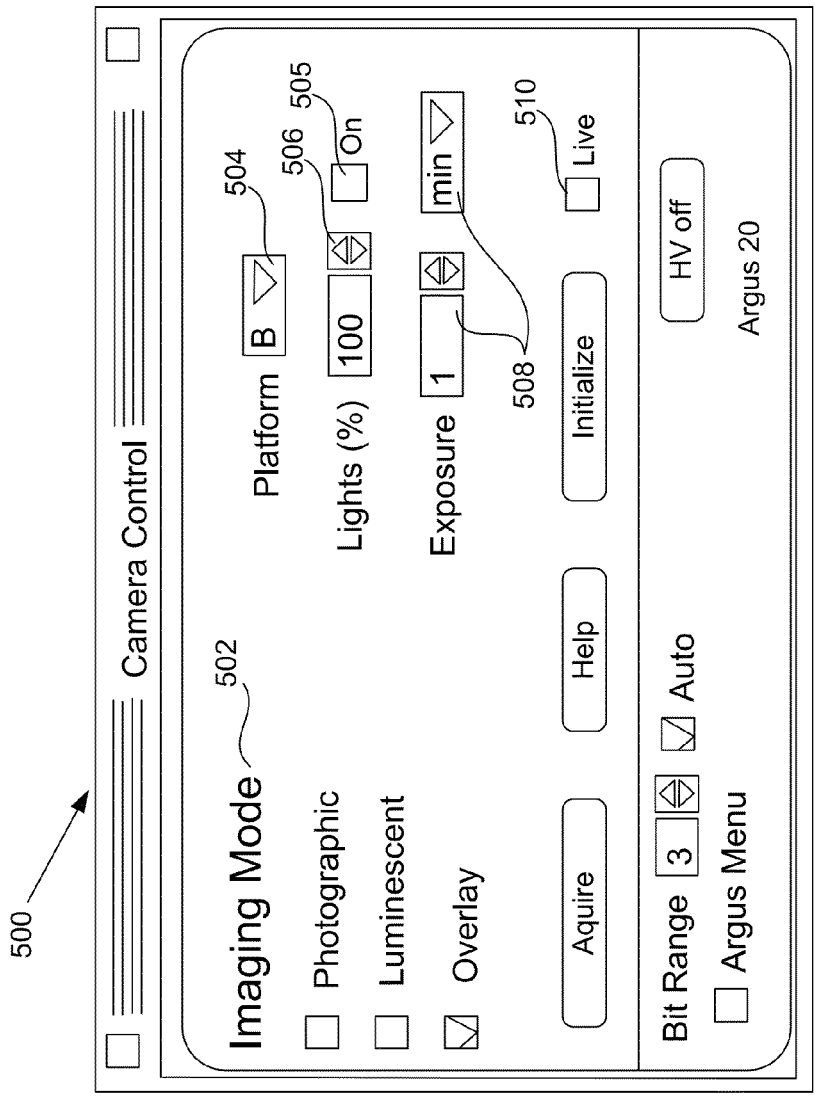
FIG. 5 illustrates an image capture graphical user interface suitable for controlling the imaging apparatus of FIG. 1.

The present invention may also include other user interface components outside of the image control/measurement window 300. By way of example, FIG. 5 illustrates an image capture GUI 500 suitable for controlling the imaging apparatus 100. The image capture GUI 500 includes an imaging mode control section 502. The imaging mode control section 502 allows the user to designate one or multiple images to be taken. The camera GUI interface 500 also provides the user with interfaces to control platform selection 504, lights on/off 505, set light strength 506 and set the exposure duration 508. The camera GUI interface 500 may also include other functionality and tools useful in obtaining an image with the imaging apparatus 100 not shown in FIG. 5. By way of example, the camera GUI interface 500 may also include control for manipulating the photon threshold for registering a pixel in the luminescence representation. Correspondingly, the photon threshold may be used to reduce electronic noise when capturing the luminescence representation.

Figure 6A:
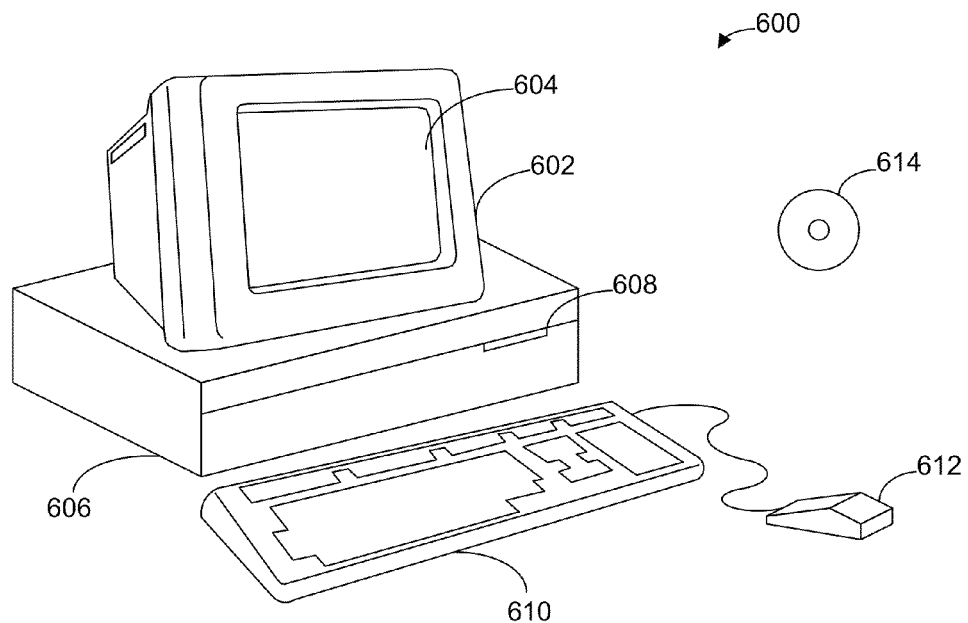
FIGS. 6A and 6B illustrate a computer system suitable for implementing embodiments of the present invention.
Figure 6B:
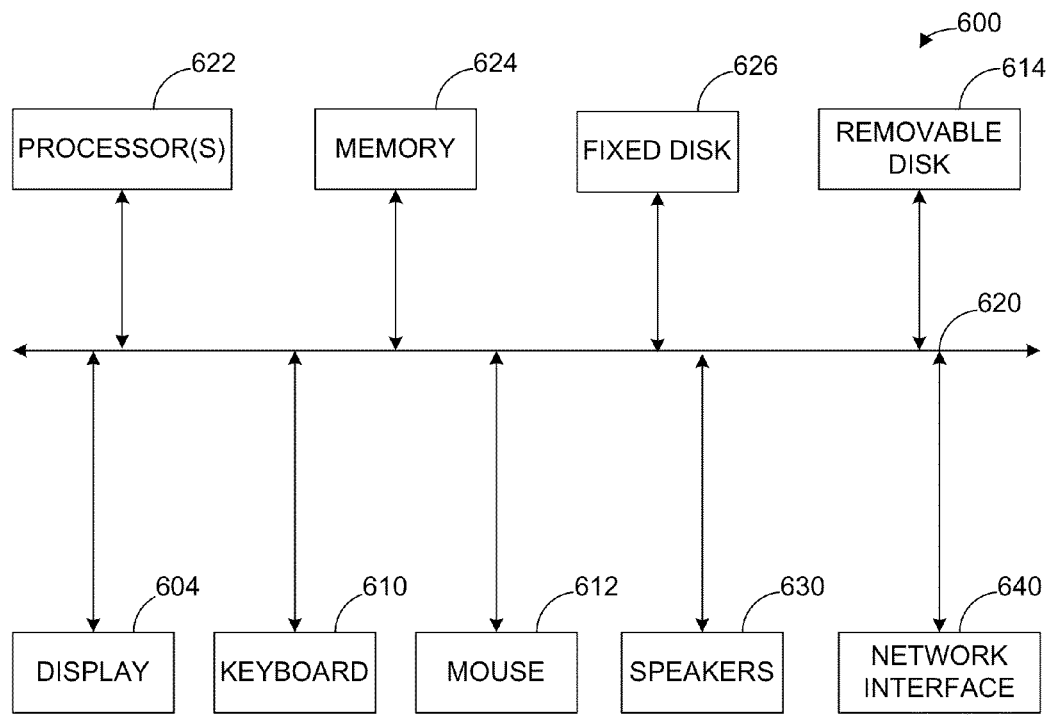

FIGS. 6A and 6B illustrate a computer system 600 suitable for implementing embodiments of the present invention. FIG. 6A shows one possible physical form of the computer system. Of course, the computer system may have many physical forms ranging from an integrated circuit, a printed circuit board and a small handheld device up to a huge super computer. Computer system 600 includes a monitor 602, a display 604, a housing 606, a disk drive 608, a keyboard 610 and a mouse 612. Disk 614 is a computer-readable medium used to transfer data to and from computer system 600.

FIG. 6B is an example of a block diagram for computer system 600. Attached to system bus 620 are a wide variety of subsystems. Processor(s) 622 (also referred to as central processing units, or CPUs) are coupled to storage devices including memory 624. Memory 624 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A fixed disk 626 is also coupled bi-directionally to CPU 622; it provides additional data storage capacity and may also include any of the computer-readable media described below. Fixed disk 626 may be used to store programs, data and the like and is typically a secondary storage medium (such as a hard disk) that is slower than primary storage. It will be appreciated that the information retained within fixed disk 626, may, in appropriate cases, be incorporated in standard fashion as virtual memory in memory 624. Removable disk 614 may take the form of any of the computer-readable media described below.

CPU 622 is also coupled to a variety of input/output devices such as display 604, keyboard 610, mouse 612 and speakers 630. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. CPU 622 optionally may be coupled to another computer or telecommunications network using network interface 640. With such a network interface, it is contemplated that the CPU might receive information from the network, or might output information to the network in the course of performing the above-described method steps. Furthermore, method embodiments of the present invention may execute solely upon CPU 622 or may execute over a network such as the Internet in conjunction with a remote CPU that shares a portion of the processing.

In addition, embodiments of the present invention further relate to computer storage products with a computer-readable medium that have computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher level code that are executed by a computer using an interpreter.

Although the present invention has been discussed primarily in the context of making measurements for the summation of photon counts within the image measurement window 301, the present invention is suitable for other imaging applications and may be tailored correspondingly. By way of example, the present invention may be adapted for analysis of high detail in-vivo applications and thus may include zoom tools in the display function section 314. Other applications may implement global image processing procedures well known in the image processing arts. For example, binning may be implemented to account for insufficient information per pixel. More specifically, the number of pixels in each direction of the luminescence representation may be halved to produce a new pixel array comprising the magnitude of four previous pixels in a single new pixel to improve statistical analysis. Although various details have been omitted for brevity's sake, obvious design alternatives may be implemented. Therefore, the present examples are to be considered as illustrative and not restrictive, and the invention is not to be limited to the details given herein, but may be modified within the scope of the appended claims.

What is claimed is:

1. A system comprising:
a display unit;
one or more processors configured to display an image and associated information on the display unit, wherein the image comprises an external representation of at least a portion of an object superimposed with a light representation, the light representation corresponding to the location and magnitude of electro-magnetic radiation emitted from an internal portion of the object; and
a graphical user interface running on one or more of the processors and providing the image on the display,
wherein the graphical user interface further comprises a first selectable tool for defining a region of interest on the image and a second selectable tool for performing a measurement on the defined region of interest; and
wherein the one or more processors are configured so that when a user activates the second tool, the one or more processors calculate information about a portion of the image within the defined region of interest.

2. The system of claim 1, wherein the first tool comprises a button that, when activated, displays a region of interest on the displayed image.

3. The system of claim 1, wherein the light representation comprises in-vivo light data from at least one mammalian specimen.

4. The system of claim 1, wherein the graphical user interface comprises a visual manipulation tool that, when activated, allows the user to adjust threshold magnitudes of the electro-magnetic radiation corresponding to the light representation.

5. The system of claim 1, wherein the light representation comprises data obtained from using a live imaging mode to measure radiation emitted from the object.

6. The system of claim 1, wherein the graphical user interface comprises an electronic notebook space for displaying text information pertaining to the image.

7. A method for analyzing a region of interest of an image presented on a display, the method comprising:
using an electronic processor to define a region of interest on the image by providing a first input to the electronic processor, wherein providing the first input comprises selecting an activatable region of interest tool on a graphical user interface presented on the display such that the region of interest tool and the image are concurrently displayed on the display, the image comprising an external representation of an object superimposed with a light representation, the light representation corresponding to the location and magnitude of electro-magnetic radiation emitted from the object; and using the electronic processor to calculate a property of the image within the region of interest by providing a second input to the electronic processor, wherein providing the second input comprises selecting an activatable measurement tool on the graphical user interface.

8. The method of claim 7, wherein the light representation comprises light emission data.

9. The method of claim 7, further comprising using the electronic processor to define the region of interest by activating the region of interest tool to at least one of position and reshape the region of interest on the image to define boundaries within which the property is calculated.

10. The method of claim 7, further comprising using the electronic processor to display an electronic notebook on the display concurrently with the region of interest tool and the image, and to display the calculated property of the image within the region of interest in the electronic notebook.

11. The method of claim 10, further comprising using the electronic processor to display user notes about an experiment or imaged object in the electronic notebook.

12. The method of claim 7, wherein the light representation comprises in-vivo light data from at least one mammalian specimen.

13. The system of claim 6, wherein the graphical user interface further comprises a third selectable tool for recording information about the image, and wherein the one or more processors are configured so that when a user activates the third tool, the one or more processors display information about the image in the electronic notebook space.

14. The system of claim 1, wherein the first selectable tool is configured so that by activating the first tool, a user can define multiple regions of interest in the image.

15. The system of claim 14, wherein the graphical user interface further comprises a fourth selectable tool for designating one of the multiple regions of interest, and wherein the one or more processors are configured so that when a user activates the fourth tool, the one or more processors calculate information about a portion of the image within the designated one of the multiple regions of interest.

* * * * *